United States Patent
Mann et al.

(10) Patent No.: US 11,376,214 B2
(45) Date of Patent: Jul. 5, 2022

(54) COMPOSITIONS AND METHODS FOR TREATMENT OF OCULAR DISEASES

(71) Applicant: KIORA PHARMACEUTICALS, INC., Salt Lake City, UT (US)

(72) Inventors: Brenda K. Mann, Salt Lake City, UT (US); Hee-Kyoung Lee, Salt Lake City, UT (US)

(73) Assignee: KIORA PHARMACEUTICALS, INC., Salt Lake City, UT (US)

( * ) Notice: Subject to any disclaimer, the term of this patent is extended or adjusted under 35 U.S.C. 154(b) by 0 days.

(21) Appl. No.: 16/863,753

(22) Filed: Apr. 30, 2020

(65) Prior Publication Data

US 2020/0345634 A1 Nov. 5, 2020

Related U.S. Application Data

(60) Provisional application No. 62/842,995, filed on May 3, 2019.

(51) Int. Cl.

| | |
|---|---|
| *A61K 9/00* | (2006.01) |
| *A61K 31/4709* | (2006.01) |
| *A61K 31/55* | (2006.01) |
| *A61K 31/7036* | (2006.01) |
| *A61K 47/36* | (2006.01) |
| *A61K 9/06* | (2006.01) |

(52) U.S. Cl.
CPC .......... *A61K 9/0051* (2013.01); *A61K 9/0048* (2013.01); *A61K 9/06* (2013.01); *A61K 31/4709* (2013.01); *A61K 31/55* (2013.01); *A61K 31/7036* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 2014/0341842 A1 | 11/2014 | Zarembinski et al. | |
| 2015/0157563 A1* | 6/2015 | Wirostko | A61K 45/06 424/428 |

OTHER PUBLICATIONS

Lee et al., Crosslinked carboxymethylated hyaluronic acid (CMHA-S)-based ocular sustained delivery of antibiotics, Investigative Ophthalmology & Visual Science Sep. 2016, vol. 57, issue 12, 1124, printed from https://iovs.arvojournals.org/article.aspx?articleid=2559820, 2 pages.*
Yang et al., Thiolated Carboxymethyl-Hyaluronic-Acid-Based Biomaterials Enhance Wound Healing in Rats, Dogs, and Horses, ISRN Vet Sci, Jan. 11, 2012, vol. 2011:851593, 8 pages.*
International Search Report and Written Opinion for International Application No. PCT/US2020/030691, dated Jul. 20, 2020, 14 pages.
Luo et al., Hyaluronan-based Sustained Delivery of the Antibiotic Besifloxacin to the Eye, Proceedings of the National Conference on Undergraduate Research (NCUR), Apr. 9, 2016, pp. 1065-1071. Retrieved from the Internet: URL: https://www.ncurproceedings.org/ojs/index.php/NCUR2016/article/view/1932 [retrieved on Jul. 8, 2020].
Wirostko et al., Ophthalmic Uses of a Thiol-Modified Hyaluronan-Based Hydrogel, Advances in Wound Care, vol. 3, No. 11, Nov. 1, 2004, pp. 708-716.

* cited by examiner

*Primary Examiner* — Gigi G Huang
(74) *Attorney, Agent, or Firm* — Medler Ferro Woodhouse & Mills PLLC

(57) ABSTRACT

The present disclosure relates to compositions and methods for treating ocular diseases with antibiotics. In particular, the disclosure relates to non-blurring, antibiotic-containing hydrogel compositions that have an extended contact time on the eye and do not interfere with wound healing.

27 Claims, 6 Drawing Sheets

COMPOSITIONS AND METHODS FOR TREATMENT OF OCULAR DISEASES

CROSS REFERENCE TO RELATED APPLICATIONS

This application claims the benefit of U.S. Provisional Application No. 62/842,995 filed May 3, 2019, entitled "Compositions and Methods for Treatment of Ocular Diseases," the entire contents of which are incorporated herein by reference.

FIELD OF THE DISCLOSURE

The disclosure relates to compositions and methods for treating ocular diseases with antibiotics. In particular, the disclosure relates to non-blurring, antibiotic-containing hydrogel compositions that have an extended contact time on the eye and do not interfere with wound healing.

BACKGROUND OF THE DISCLOSURE

Topical ophthalmic antibiotics are generally prescribed prophylactically whenever there is a wound to the eye. While these antibiotics serve to both prevent and treat any bacterial infection, they do not aid in closing the wound. To the contrary, such antibiotics may delay wound closing by interfering/inhibiting the wound healing process. Generally, such topical ophthalmic antibiotics are formulated in any of a variety of formulations such as an eye drop solution, suspension, emulsion, a gel, ointment, and the like. Unfortunately, eye drop solutions, suspensions, and emulsions do not remain in contact with the eye for more than a few minutes because they are rapidly removed from the eye via factors such as tear turnover and gravity. Gels and ointments currently used may have a slightly longer contact time, but unfortunately are often associated with blurring that interferes with a patient's vision. Thus, there is a need for non-blurring compositions and methods for treating ocular disease with antibiotics that have an extended contact time on the eye and also do not interfere with wound healing.

SUMMARY OF THE DISCLOSURE

The present disclosure provides a hydrogel that may be formulated to contain antibiotics (e.g., an antibiotic-containing hydrogel) to provide enhanced prevention/treatment of bacterial infection within the eye, while simultaneously having the properties of increasing antibiotic contact time with the surface of the eye and providing clear vision for a subject (i.e., not blurring a subject's vision). Additionally, the antibiotic-containing hydrogel disclosed herein also has the ability to aid in the wound healing process. The hydrogel is shear-thinning and comprises modified or unmodified hyaluronic acid that is covalently crosslinked.

In one aspect, the disclosure provides an ocular composition that includes a shear-thinning hydrogel and an antibiotic. In an embodiment, the sheer-thinning hydrogel may include hyaluronic acid, which may be at a concentration of between about 3 and about 10 mg/ml. It is also contemplated within the scope of the disclosure that the hyaluronic acid may be about 3, 4, 5, 6, 7, 8, 9, or 10 mg/ml, or any intervening value such as, for example, 3.0, 3.1, 3.2, 3.3, 3.4, 3.5, 3.6, 3.7, 3.8, 3.9, or 4.0 mg/ml. In an embodiment, the hyaluronic acid may be covalently crosslinked. In an embodiment, the antibiotic may be at a concentration of about 1 to about 10 mg/ml. It is also contemplated within the scope of the disclosure that the antibiotic may be about 1, 2, 3, 4, 5, 6, 7, 8, 9, or 10 mg/ml, or any intervening value such as, for example, 3.0, 3.1, 3.2, 3.3, 3.4, 3.5, 3.6, 3.7, 3.8, 3.9, or 4.0 mg/ml.

In an embodiment, the hyaluronic acid is modified or unmodified hyaluronic acid.

In an embodiment, the antibiotic has a solubility in water of about 1 mg/ml or greater.

In an embodiment, the antibiotic is a fluoroquinolone.

In an embodiment, the antibiotic is moxifloxacin or a salt of moxifloxacin.

In an embodiment, the antibiotic is moxifloxacin hydrochloride.

In an embodiment, the antibiotic is a salt of besifloxacin.

In an embodiment, the antibiotic is besifloxacin hydrochloride.

In an embodiment, the antibiotic is an aminoglycoside.

In an embodiment, the antibiotic is tobramycin.

In an embodiment, the modified hyaluronic acid is thiolated hyaluronic acid.

In an embodiment, the modified hyaluronic acid is thiolated carboxymethyl hyaluronic acid.

In an embodiment, the hydrogel may be disulfide crosslinked.

In an aspect, the disclosure provides an ocular composition that includes a shear-thinning hydrogel and an antibiotic. In an embodiment, the sheer-thinning hydrogel may include thiolated hyaluronic acid, which may be present at a concentration of between about 3 and about 10 mg/ml. It is also contemplated within the scope of the disclosure that the thiolated hyaluronic acid may be about 3, 4, 5, 6, 7, 8, 9, or 10 mg/ml, or any intervening value such as, for example, 3.0, 3.1, 3.2, 3.3, 3.4, 3.5, 3.6, 3.7, 3.8, 3.9, or 4.0 mg/ml. In an embodiment, the hyaluronic acid may be disulfide crosslinked. In an embodiment, the antibiotic may be at a concentration of about 1 to about 10 mg/ml. It is also contemplated within the scope of the disclosure that the antibiotic may be about 1, 2, 3, 4, 5, 6, 7, 8, 9, or 10 mg/ml, or any intervening value such as, for example, 3.0, 3.1, 3.2, 3.3, 3.4, 3.5, 3.6, 3.7, 3.8, 3.9, or 4.0 mg/ml.

In an embodiment, the thiolated hyaluronic acid has a thiol modification of about 0.05 to about 1.0 µmol thiol/mg. It is also contemplated within the scope of the disclosure that the thiolated hyaluronic acid has a thiol modification of about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0 µmol thiol/mg, or any intervening value such as, for example, about 0.05, 0.06, 0.07, 0.08, 0.09, or 0.1 µmol thiol/mg.

In an embodiment, the thiol modification is about 0.05 to about 0.2 µmol thiol/mg, and wherein the thiolated hyaluronic acid is at a concentration of about 6.5 to about 8.5 mg/ml. It is also contemplated within the scope of the disclosure that the thiol modification is about 0.05, 0.05, 0.1, 0.15, or 0.2 µmol thiol/mg, or any intervening value such as, for example, 0.1, 0.11, 0.12, 0.13, 0.14, or 0.15 µmol thiol/mg. It is also contemplated within the scope of the disclosure that the hyaluronic acid is at a concentration of about 6.5, 7.0, 7.5, 8.0, or 8.5 mg/ml, or any intervening value such as, for example, about 6.5, 6.6, 6.7, 6.8, 6.9, or 7.0 mg/ml.

In an embodiment, the antibiotic is a fluoroquinolone.

In an embodiment, the antibiotic is a salt of moxifloxacin.

In an embodiment, the antibiotic is moxifloxacin hydrochloride.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless otherwise clear from context, all numerical values provided herein are modified by the term "about."

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

Unless specifically stated or obvious from context, as used herein, the term "or" is understood to be inclusive. Unless specifically stated or obvious from context, as used herein, the terms "a", "an", and "the" are understood to be singular or plural.

As used herein, the term "shear-thinning" refers to a state in which viscosity decreases as shear rate increases, thereby indicating shear-thinning behavior.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect (e.g., reducing or eliminating a bacterial infection). The effect can be prophylactic in terms of completely or partially preventing a disease or infection or symptom thereof and/or can be therapeutic in terms of a partial or complete cure for a disease or infection and/or adverse effect attributable to the disease or infection. "Treatment," as used herein, covers any treatment of a disease or condition or infection (e.g., an ocular infection) in a mammal, particularly in a human, and includes: preventing the disease or infection from occurring in a subject which can be predisposed to the disease or infection but has not yet been diagnosed as having it; inhibiting the disease or infection (e.g., arresting its development, relieving the disease or infection, reducing or eliminating a bacterial infection, and the like).

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methylamine, dimethylamine, trimethylamine, triethlyamine, ethylamine, and the like. (See, for example, S. M. Barge et al., "Pharmaceutical Salts," J. Pharm. Sci., 1977, 66:1-19 which is incorporated herein by reference.). Salts that are known to be compatible with various antibiotics are specifically contemplated within the scope of the disclosure.

Ranges can be expressed herein as from "about" one particular value and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. In this regard, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "therapeutically effective amount" of an agent described herein is an amount sufficient to provide a therapeutic benefit in the treatment of a condition or to delay or minimize one or more symptoms associated with the condition (e.g., an amount sufficient to reduce or eliminate a bacterial infection in an eye of a subject). A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

Where applicable or not specifically disclaimed, any one of the embodiments described herein are contemplated to be able to combine with any other one or more embodiments, even though the embodiments are described under different aspects of the disclosure.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

These and other embodiments are disclosed and/or encompassed by, the following detailed description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 2A shows a graph of Moxifloxacin-HCl release from hydrogel (blue circles) or PBS (green circles) in the medi-dialysis chamber over time. FIG. 2B shows the graph of Moxifloxacin-FB release from hydrogel (blue circles) or PBS (green circles) in the medi-dialysis chamber over time. The hydrogel had a CMHA-S concentration of about 7.5 mg/ml.

FIG. 4A shows the graph of Besifloxacin-HCl release from hydrogel (blue diamonds) or PBS (green circles) in the mini-dialysis chamber over time. FIG. 4B shows the graph of Moxifloxacin-FB release from hydrogel ("OBG") or PBS in a mini-dialysis chamber over time. The hydrogel had a CMHA-S concentration of about 7.5 mg/ml.

FIG. 5A shows a plate presenting results for a ZOI study against the gram-positive bacterial strain, *Staphylococcus aureus* (*S. aureus*). FIG. 5B shows a plate presenting results for a ZOI study against the gram-negative bacterial strain *Pseudomonas aeruginosa* (*P. aeruginosa*). On each plate, samples from PBS plus drug are on the left half and samples from hydrogel ("OBG") plus drug are on the right half.

FIG. 6A shows the concentration in aqueous humor; FIG. 6B shows the concentration in cornea; and FIG. 6C shows the concentration in conjunctiva. N=10; error bars represent standard deviation.

DETAILED DESCRIPTION OF THE DISCLOSURE

Figure 1:
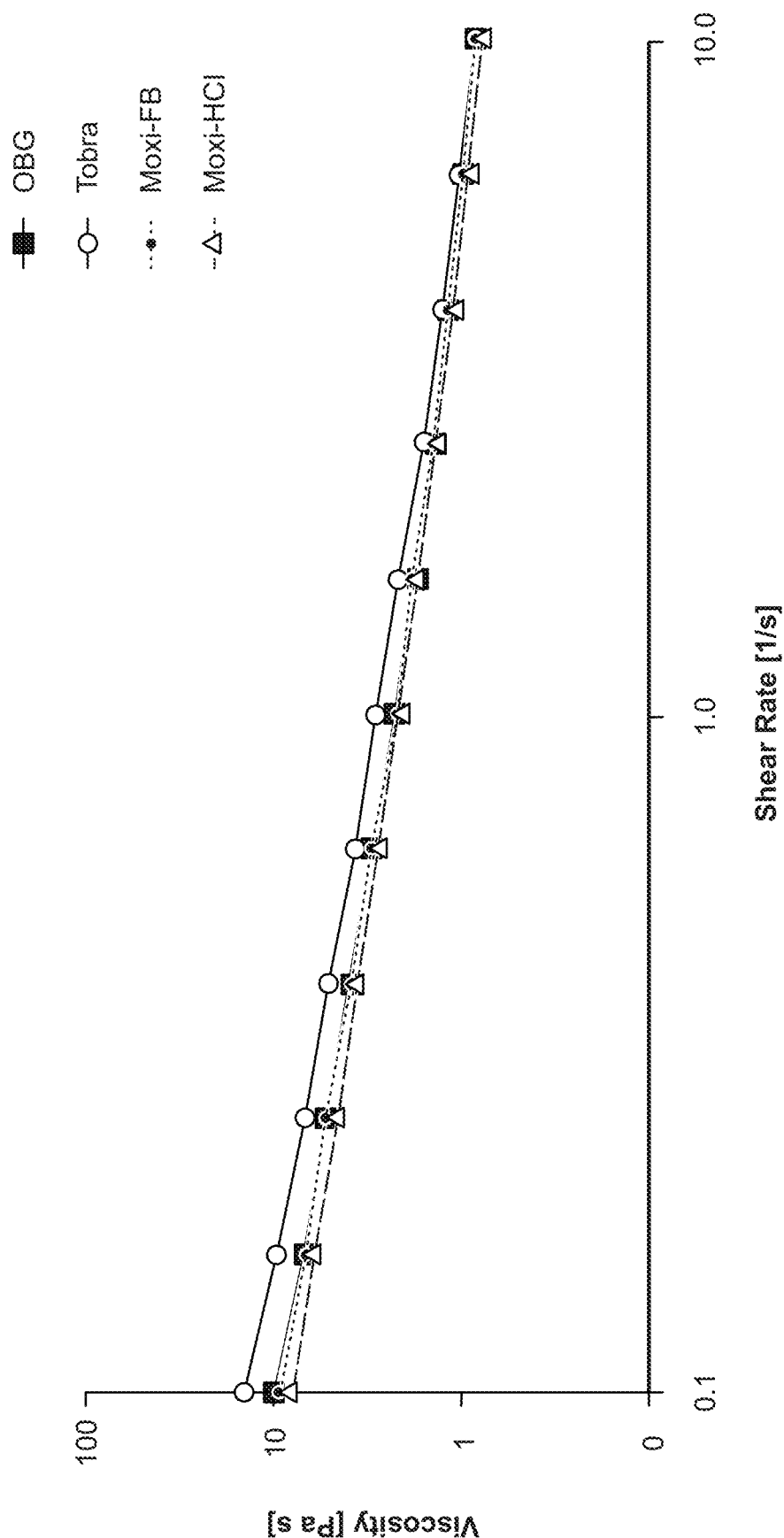
FIG. 1 is a graph depicting viscosity as a function of shear rate of hydrogel ("OBG") alone (black squares) or with antibiotic (1 mg/ml) incorporated (red, blue, green circles).

The present disclosure is based, at least in part, on the discovery that a hydrogel may be formulated to contain antibiotics (e.g., an antibiotic-containing hydrogel) to provide enhanced prevention/treatment of bacterial infection within the eye, while simultaneously having increased contact time with the surface of the eye in a way that allows the subject to have clear vision (e.g., does not blur a subject's vision). The present disclosure provides an antibiotic-containing hydrogel formulated in an exemplary embodiment as an eye drop. Advantageously, the antibiotic-containing hydrogel is formulated to be non-blurring while having extended contact time with the surface of the eye, which provides beneficial effects in terms of prophylactically preventing or treating a bacterial infection. Moreover, the antibiotic-containing hydrogel disclosed herein does not delay or prevent the process of wound healing in an eye of a subject. Additionally, the antibiotic-containing hydrogel disclosed herein also has the ability to aid in the wound healing process. The hydrogel is shear-thinning and comprises modified or unmodified hyaluronic acid that is covalently crosslinked. In one aspect, the antibiotic has a solubility in water of at least about 1 mg/ml or greater. In another aspect, the antibiotic is a fluoroquinolone. The techniques herein provide a number of advantages over the prior art, including: enhanced residence time on the surface of the high, a non-blurring ophthalmic formulation, and the ability to reduce inhibition of wound healing.

Compounds of the Disclosure

An ocular composition in the form of a hydrogel is provided that incorporates an antibiotic. The hydrogel is a covalently crosslinked hyaluronic acid, and the hyaluronic acid may be modified or unmodified. Unmodified hyaluronic acid may be covalently crosslinked by a variety of methods, including crosslinking using 1,4-butanediol diglycidyl ether (BDDE), divinylsulfone, and dihydrazide. The hyaluronic acid may be modified to change the charge of the molecule, change its biological activity, or to include groups that may be used for crosslinking purposes. Particularly useful are thiolated hyaluronic acid or thiolated carboxymethyl hyaluronic acid. Modified hyaluronic acid may be crosslinked with an external molecule for crosslinking, or without an external crosslinker molecule. For crosslinking thiolated HA or CMHA, a molecule with thiol-reactive sites, such as acrylates, methacrylates, haloacetates, haloacetamides, or maleimides, may be used as an external crosslinker molecule, examples of which include poly(ethylene glycol) diacrylate and poly(ethylene glycol) bisbromoacetate. For crosslinking without an external crosslinker molecule, in particular, thiolated HA or CMHA may be disulfide crosslinked via an oxidation process. Such disulfide crosslinking may be aided by use of an oxidant such as sodium hypochlorite or peroxide.

When modified HA is crosslinked via the modification (e.g., disulfide crosslinking of thiolated HA), the level of modification may be adjusted to control the amount of crosslinking of the hydrogel, such that a higher level of modification leads to more crosslinking. Particularly useful for formulating hydrogels of the present disclosure is thiolated HA or thiolated CMHA, where the thiol modification is about 0.05 to about 1.0 μmol thiol per mg of HA or CMHA. Modification levels within this range are particularly suitable for forming crosslinked hydrogels with a desired shear-thinning profile and viscosity.

When placed on the surface of the eye, shear-thinning hydrogels made using thiolated CMHA and having a concentration range of about 3 to about 10 mg/ml remain in contact with the eye surface for at least 30 minutes and up to about 2 hours.

Combination Treatments

The antibiotic-containing hydrogel compositions and methods described herein may be used to direct the administration of combination antibiotic therapies to treat particular bacterial infections (e.g., ocular bacterial infections). In order to increase the effectiveness of a treatment with the compositions of the present disclosure, e.g., an antibiotic selected and/or administered as a single agent, or to augment the protection of another therapy (second therapy), it may be desirable to combine these compositions (e.g., include more than one antibiotic in the antibiotic-containing hydrogel compositions) and methods with one another, or with other agents and methods effective in the treatment, amelioration, or prevention of diseases and pathologic conditions, for example, an antibiotic infection.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary.

Pharmaceutical Compositions

Antibiotics that may be incorporated in the antibiotic-containing hydrogel compositions disclosed herein are those that are clinically relevant for ocular conditions and may include aminoglycosides, penicillins, cephalosporins, fluoroquinolones, macrolides, and combinations thereof. Particularly useful in the present disclosure are antibiotics that have a solubility in water of at least about 1 mg/ml. Therefore, salts of fluoroquinolones that increase their solubility in water, such as moxifloxacin hydrochloride and besifloxacin hydrochloride, are particularly suitable. An exemplary aminoglycoside that may be used is tobramycin. The antibiotic may be incorporated at a concentration of about 1 to 10 mg/ml and may be incorporated prior to, during, or after crosslinking of the hydrogel. The concentration of the antibiotic in the hydrogel may be on the same order as the solubility of the antibiotic in water or even higher, with the concentration being up to about 10 times that of the solubility.

Method of Treatment

The topical application of an antibiotic can be used to treat or prevent a variety of conditions associated with ocular infection. For example, conditions of the lids including blepharitis, blepharconjunctivies, meibomianitis, acute or chronic hordeolum, chalaziori, dacryocystitis, dacryoadenities, and acne rosacea; conditions of the conjunctiva including conjunctivitis, ophthalmia neonatorum, and trachoma; conditions of the corea including corneal ulcers, superficial and interstitial keratitis, keratoconjunctivitis, foreign bodies, and post-operative infections; and conditions of the anterior chamber and uvea including endophthalmitis, infectious uveitis, and post-operative infections, are a few of the tissues and conditions that can be treated by topical application of an antibiotic. The prevention of infection includes preoperative treatment prior to surgery as well as other suspected infectious conditions or contact.

Examples of prophylaxis situations include treatment prior to surgical procedures such as blepharoplasty, removal of chalazia, tarsorrhapy, procedures for the canualiculi and lacrimal drainage system and other operative procedures involving the lids and lacrimal apparatus; conjunctival surgery including removal of ptyregia, pingueculae and tumors, conjunctival transplantation, traumatic lesions such as cuts, burns and abrasions, and conjunctival flaps; corneal surgery including removal of foreign bodies, keratotomy, and corneal transplants; refractive surgery including photorefractive procedures; glaucoma surgery including filtering blebs; paracentesis of the anterior chamber; iridectomy; cataract surgery; retinal surgery; and procedures involving the extraocular muscles. The prevention of ophthalmia neonatorum is also included.

More generally, antibiotics can be used to treat or prevent ocular infections caused by a variety of bacteria or parasites, including but not limited to one or more of the following organisms: *Staphylococcus* including *Staphylococcus aureus* and *Staphylococcus epidermidis*; *Streptococcus* including *Streptococcus pneumoniae* and *Streptococcus pyogenes* as well as Streptococci of Groups C, F, and G and *Viridans* group of Streptococci; *Haemophilus* influenza including biotype III *Aegyptius*); *Haemophilus ducreyi*; *Moraxella catarrhalis*; *Neisseria* including *Neisseria gonorrhoeae* and *Neisseria meningitidis*; *Chlamydia* including *Chlamydia trachomatis, Chlamydia psittaci*, and *Chlamydia pneumoniae*; *Mycobacterium* including *Mycobacterium tuberculosis* and *Mycobacterium avium*-intracellular complex as well as atypical *mycobacterium* including *M. marinum, M. fortuitm*, and *M. chelonae*; *Bordetella pertussis*; *Campylobacter jejuni*; *Legionella pneumophila*; *Bacteroides bivius*; *Clostridium perfringens*; *Peptostreptococcus* species; *Borrelia burgdorferi*; *Mycoplasma pneumoniae*; *Treponema pallidum*; *Ureaplasma urealyticum*; *Toxoplasma*; malaria; and *Nosema*.

The agents contained in the disclosed drug delivery systems will be released from the antibiotic-containing hydrogel compositions at rates that depend on such factors as the drug itself and its physical form, the extent of drug loading and the pH of the system.

The antibiotics used in the present invention are commercially available or readily obtained by a worker skilled in the art through known reactions techniques. The antibiotic can be combined with the other ingredients in the chosen dosage form by conventional methods known in the art.

The antibiotic-containing hydrogel composition is topically applied to an eye of a human or non-human animal, the latter including cows, sheep, horses, pigs, goats, rabbits, dogs, cats, and other mammals. The composition can be topically applied, without limitation, to the front of the eye, under the upper eyelid, on the lower eyelid and in the cul-de-sac. The application can be as a treatment of an infection in the eye or as a preventive such as prior to surgery.

Kits

In general, antibiotic-containing hydrogel compositions of the invention may be provided as a kit that contains the antibiotic or compositions of the invention packaged to facilitate dispensing and/or applying the composition to affected or susceptible regions of the eye. The packaging or dispenser may include a dropper, bottle, tube, spray bottle, or other dispenser and instructions for use.

The kits are manufactured using medically acceptable conditions and contain components that have sterility, purity and preparation that is pharmaceutically acceptable.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a class bacterial infections, in a subject. Instructions may be provided for practicing any of the methods described herein.

The kits of this disclosure are in suitable packaging. Suitable packaging includes, but is not limited to, droppers, vials, bottles, jars, flexible packaging (e.g., sealed Mylar or plastic bags), and the like. The container may further comprise a second pharmaceutically active agent.

Kits may optionally provide additional components such as buffers and interpretive information. Normally, the kit comprises a container and a label or package insert(s) on or associated with the container.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

EXAMPLES

The present disclosure is further illustrated by the following examples, which should not be construed as limiting. The contents of all references, published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Example 1: Hydrogel Formation

Thiol-modified carboxymethyl HA (CMHA-S) was synthesized as described in Lawyer et al. [1] and Wendling et al. [2], with a thiol modification of 0.1, 0.2, 0.4, or 0.7 μmol thiol/mg. Hydrogels were created by dissolving CMHA-S in phosphate-buffered saline (PBS; pH 7.4). The CMHA-S was disulfide crosslinked under continuous mixing with the addition of sodium hypochlorite. Rheological testing was performed using a parallel plate format rheometer with a 25 mm-diameter stainless steel geometry. Samples (5-6 ml) of hydrogel were placed in a 35 mm Petri dish, and the geometry was lowered to a gap of 5 mm. To determine viscosity and shear-thinning, the shear rate was varied from 0.1 to 10 Hz. A decreasing viscosity as shear rate increases indicates shear-thinning behavior. Table 1 provides the thiol modification of the CMHA-S, concentration of CMHA-S, and resultant viscosity of the hydrogel (at 2.5 Hz) for 4 hydrogel formulations. All 4 formulations displayed shear-thinning behavior.

TABLE 1

Examples of hydrogel formulations and viscosity.

| Hydrogel # | Thiol modification (μmol thiol/mg) | CMHA-S concentration (mg/ml) | Viscosity at 2.5 Hz (Pa · s) |
|---|---|---|---|
| 1 | 0.12 | 8.3 | 2.6 |
| 2 | 0.15 | 7.8 | 3.6 |
| 3 | 0.13 | 7.3 | 2.4 |
| 4 | 0.39 | 4.0 | 0.9 |

Example 2: Antibiotic-Containing Hydrogels

Antibiotics were mixed into a hydrogel made as in Example 1, with a thiol modification about 0.1 μmol thiol/mg and CMHA-S concentration about 7.5 mg/ml, and having an antibiotic concentration of 1, 5, or 10 mg/ml. Antibiotics used were moxifloxacin (free base; Moxi-FB), moxifloxacin hydrochloride (Moxi-HCl), besifloxacin hydrochloride (Besi-HCl), or tobramycin (Tobra). The solubility in water for these antibiotics are about 1, 20, 1, and >50 mg/ml, respectively. Antibiotics were added as a powder to the crosslinked hydrogel and the mixture stirred or shaken vigorously to incorporate the antibiotic throughout. The antibiotic dissolved in the hydrogel or was dispersed throughout.

Example 3: Physical Properties of Antibiotic-Containing Hydrogels

Viscosity, pH, and refractive index (RI) were measured for hydrogels described in Example 2 with and without antibiotic incorporated. In this example, Moxi-HCl, Moxi-FB, or Tobramycin (1 mg/ml) were mixed into the hydrogel. Viscosity was determined as described in Example 1. RI was measured with a refractometer and pH was measured with a pH meter.

For all 3 formulations of hydrogel plus antibiotic, the shear-thinning behavior and viscosity were not significantly different than the hydrogel without drug (FIG. 1 and Table 2). The pH of hydrogel plus Moxi-HCl or Moxi-FB was similar to that of hydrogel alone, while the addition of tobramycin resulted in an increased pH (Table 2). The pH could be adjusted either before or after incorporation of the drug as needed to achieve a desired pH of about 6-8 for ophthalmic conditions. RI remained unchanged for all three mixtures of hydrogel plus antibiotic compared to hydrogel alone and are similar to the RI for deionized water (1.3326).

TABLE 2

Viscosity, RI, and pH of hydrogels with and without antibiotic (1 mg/ml) incorporated.

| Drug incorporated | Viscosity at 2.5 Hz (Pa · s) | Refractive index | pH |
|---|---|---|---|
| None | 1.5 | 1.3353 | 7.4 |
| Moxi-HCl | 1.6 | 1.3355 | 7.0 |
| Moxi-FB | 1.4 | 1.3356 | 7.4 |
| Tobramycin | 1.4 | 1.3355 | 8.6 |

Example 4: Release of Antibiotics from Hydrogels

Figure 2A:
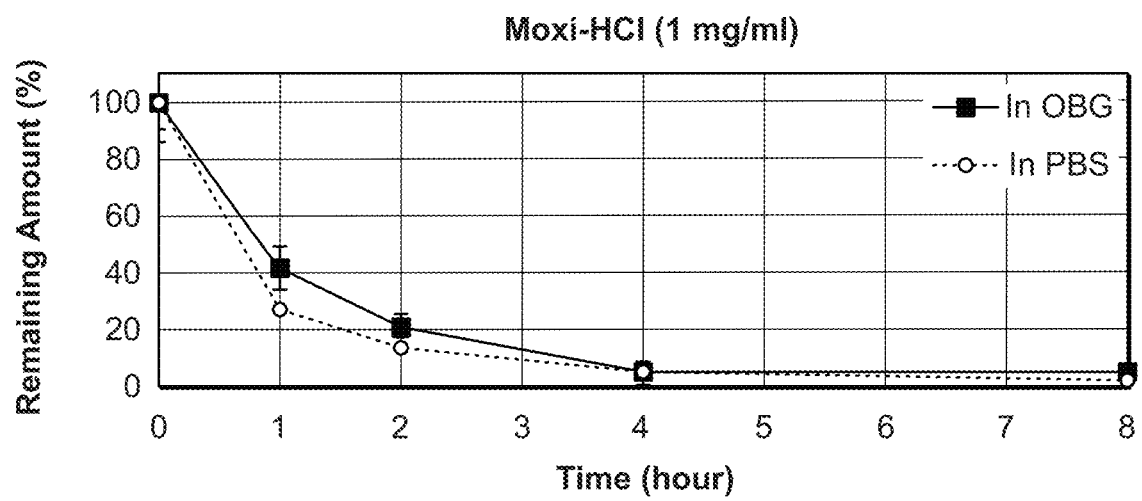
FIGS. 2A and 2B present graphs showing the release of two forms of Moxifloxacin in hydrogel ("OBG") or PBS in a medi-dialysis chamber (MWCO, 50 kDa) over time.
Figure 2B:
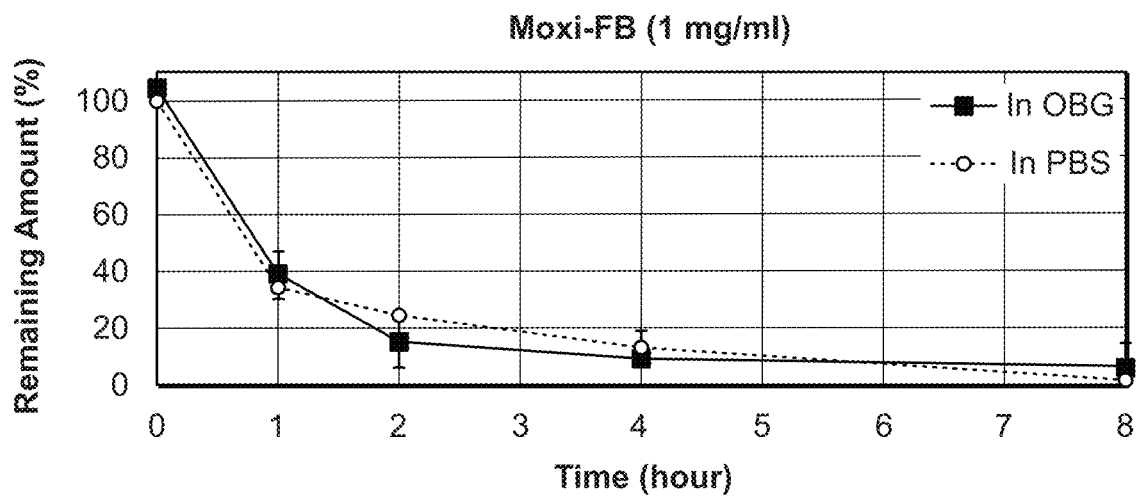

For the hydrogels with Moxi-HCl or Moxi-FB incorporated (1 mg/ml) described in Example 3, release of the drug from the hydrogel was monitored over 24 hours and compared to release of the drug from solution in PBS. For this assessment, a 0.5 ml sample of hydrogel plus drug or PBS plus drug was placed into a medi-dialysis chamber, and the chamber was placed in a beaker containing 100 ml of PBS. The remaining amount of drug in the dialysis chamber was monitored using UV spectroscopy at various time points. Compared with PBS, the hydrogel only slightly slowed down the drug release, and the dialysis was completed within 4-8 hours (FIGS. 2A and 2B).

Figure 3:
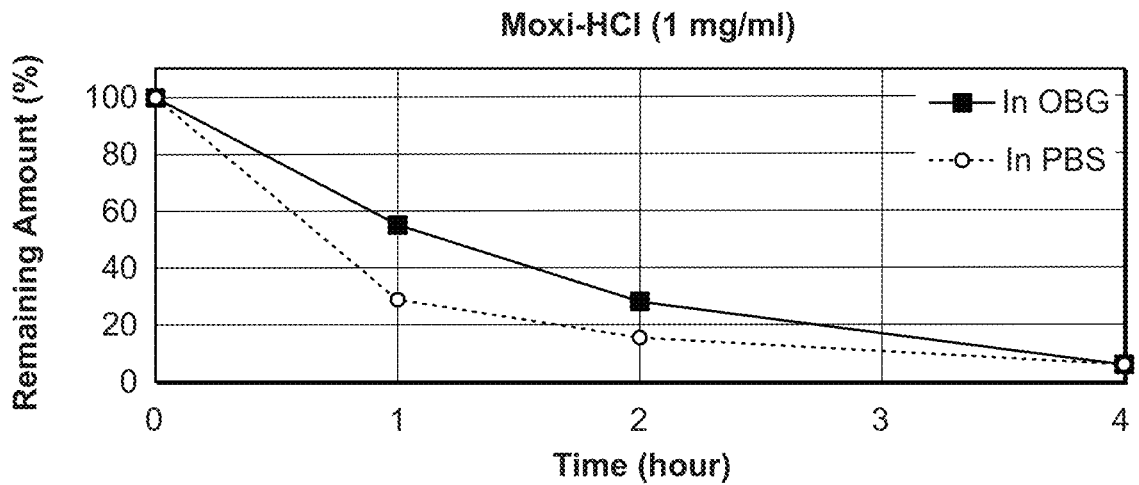
FIG. 3 shows a graph of Moxifloxacin-HCl release from hydrogel ("OBG") (blue circles) or PBS (green circles) in a medi-dialysis chamber (MWCO, 50 kDa) over time. The hydrogel had a CMHA-S concentration of about 4.0 mg/ml.

A drug release study was performed in the same manner, except for hydrogel #4 from Example 1 with Moxi-HCl incorporated at 1 mg/ml. The release was monitored as described above. As with the hydrogels having a higher concentration of CMHA-S, drug release was slightly slower from the hydrogel than from PBS, but here the release was complete within 4 hours (FIG. 3).

Figure 4A:
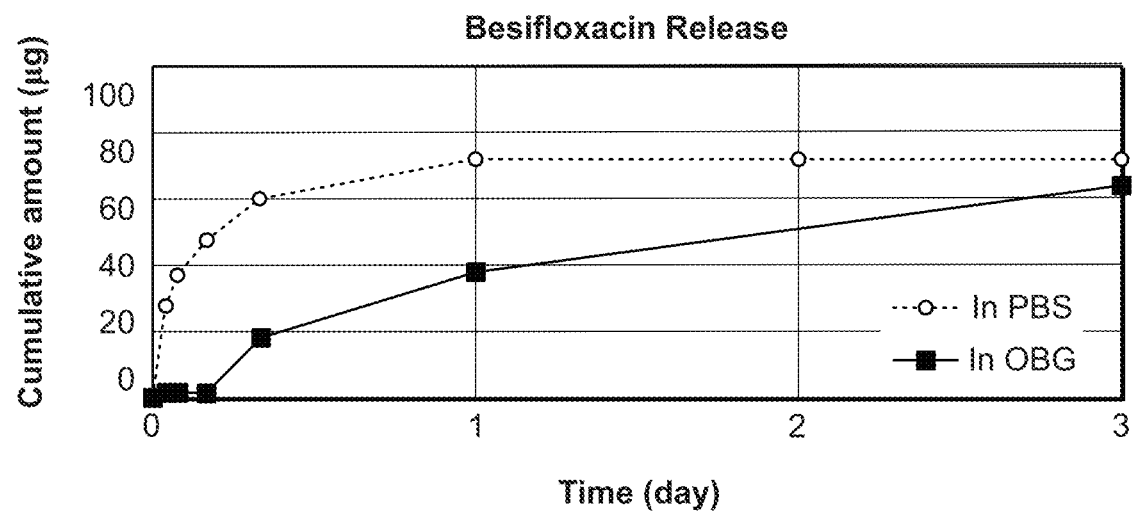
FIGS. 4A and 4B show graphs of the release of two different antibiotics from hydrogel ("OBG") (blue diamonds) or PBS (green circles) in a mini-dialysis chamber (MWCO, 50 kDa) over time.
Figure 4B:
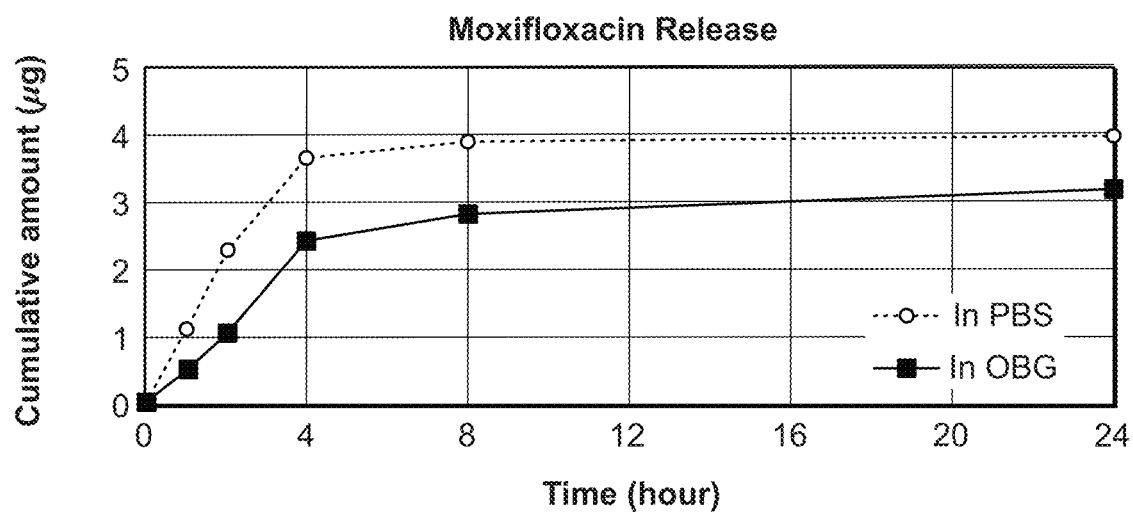

Another drug release study was performed, with Moxi-FB and Besi-HCl as the antibiotics, a hydrogel with 7.5 mg/ml CMHA-S, and the antibiotics incorporated at 10 mg/ml. For this study, the samples were placed in a dialysis chamber that was then placed in a tube that contained 10 ml of PBS. The dialysis chamber was transferred to a new tube at each time point, and the dialysate was analyzed by UV absorption (rather than the material inside the dialysis chamber), and the released amount of drug was calculated (rather than the amount remaining). In this experimental set-up, drug release from the hydrogel was slower than from PBS (FIGS. 4A and 4B). Despite the poor water solubility of Besi-HCl compared to Moxi-FB, Besi-HCl was still released from the hydrogel.

Example 5: Efficacy of Antibiotics from Hydrogels

Figure 5A:
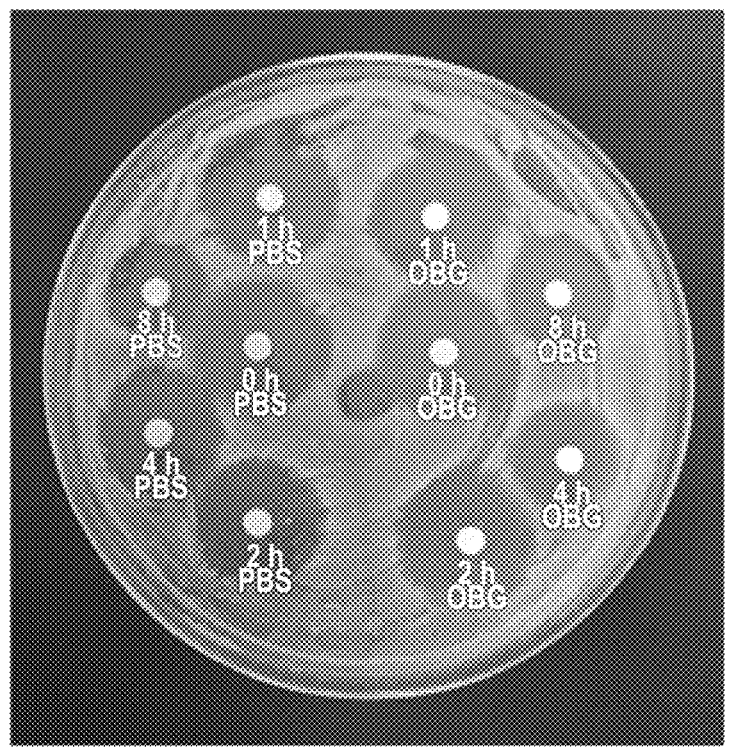
FIGS. 5A and 5B depict plates showing the results of zone of inhibition (ZOI) studies against two strains of bacteria.
Figure 5B:
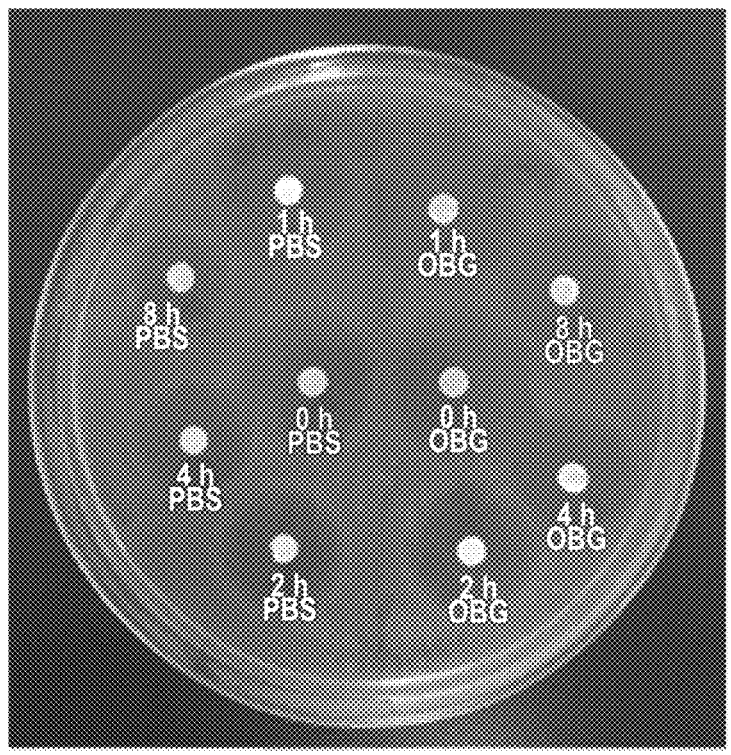

To verify the efficacy of a drug in the hydrogel, zone of inhibition (ZOI) studies were conducted. Moxi-HCl was dissolved in PBS or hydrogel (CMHA-S concentration 7.5 mg/ml) at 1 mg/ml and placed in a medi-dialysis chamber for release, as in Example 4. Samples of the dialysate were collected at 0, 1, 2, 4, and 8 hours. Filter paper disks were soaked in each sample, placed on a bacteria-inoculated plate, and the ZOIs were compared between PBS group and hydrogel group. The ZOI results against a gram-positive strain, *Staphylococcus aureus*, and a gram-negative strain, *Pseudomonas aeruginosa*, are shown in FIGS. 5A, 5B, and Table 3. The ZOIs were similar or larger for samples from the hydrogel plus drug compared to PBS plus drug, indicating that similar amounts of drug were released and remained effective even after incorporation into and release from the hydrogel.

TABLE 3

Zones of inhibition for Moxi-HCl released from PBS or hydrogel at various time points against *S. aureus* and *P. aeruginosa*.

| ZOI (mm) | Time (hrs) | | | | |
|---|---|---|---|---|---|
| | 0 | 1 | 2 | 4 | 8 |
| *S. aureus* | | | | | |
| PBS group | 32.7 ± 0.6 | 30.5 ± 2.1 | 28.3 ± 1.0 | 26.5 ± 2.5 | 23.5 ± 2.8 |
| Hydrogel group | 32.3 ± 1.4 | 31.8 ± 3.8 | 31.3 ± 1.3 | 29.8 ± 2.1 | 27.2 ± 1.3 |
| *P. aeruginosa* | | | | | |
| PBS group | 32.3 ± 3.1 | 31.7 ± 1.5 | 29.8 ± 3.8 | 24.7 ± 2.8 | 20.5 ± 1.8 |
| Hydrogel group | 31.2 ± 0.6 | 28.7 ± 0.3 | 30.5 ± 0.8 | 26.8 ± 1.4 | 26.5 ± 3.2 |

Example 6: Antibiotic-Containing Hydrogels in Rabbits

Ocular distribution of Moxifloxacin was assessed after topical administration of hydrogel plus Moxi-HCl (5 mg/ml) compared to a commercially available formulation (also 5 mg/ml of Moxi-HCl, in solution) in New Zealand White (NZW) rabbits. Thirty female NZW rabbits were treated with one of the two test articles, hydrogel+Moxi or Vigamox, via single topical ophthalmic administration into both eyes. Both test articles were administered at a dose of 0.15 mg/eye of moxifloxacin. No adverse health effects from test article administration were observed. Five animals from each group were euthanized at 0.5, 1, and 2 hours post-dose and aqueous humor, cornea, and bulbar conjunctiva were collected. Tissues were analyzed by LC-MS/MS moxifloxacin.

Figure 6A:
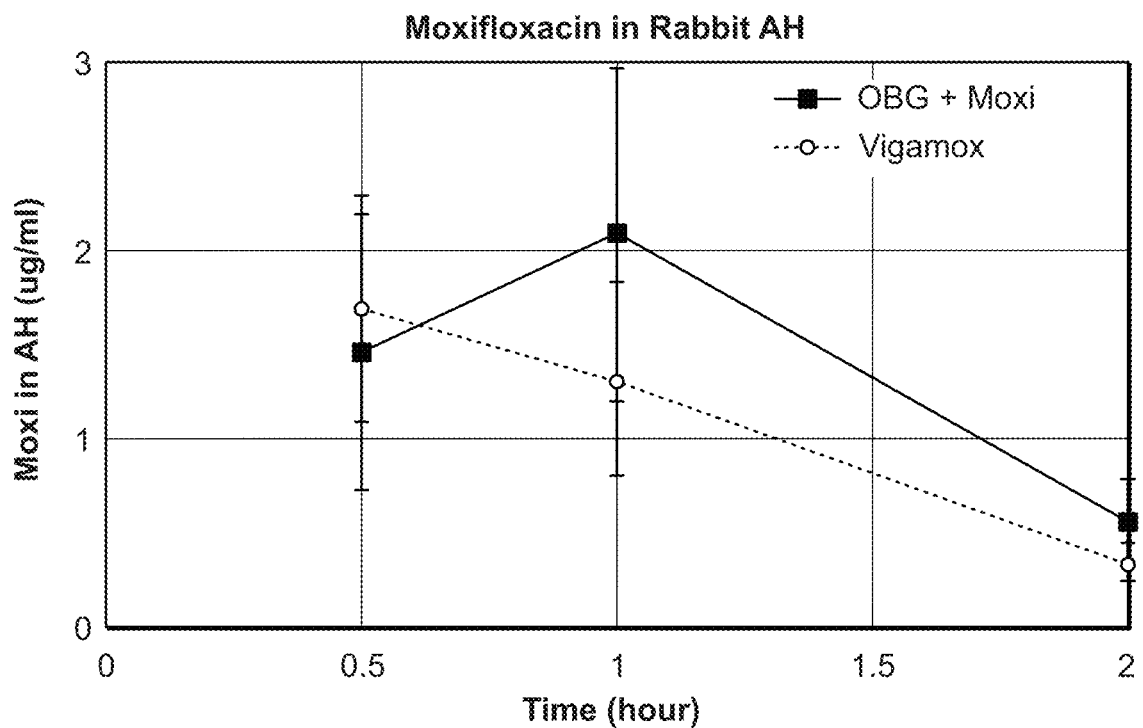
FIGS. 6A, 6B, and 6C present graphs of Moxifloxacin concentrations in different tissues of the eye over time following a single topical application in rabbits of hydrogel ("OBG") plus Moxi-HCl (blue circles) or a solution ("Vigamox") of Moxi-HCl (red circles), both at 5 mg/ml.
Figure 6B:
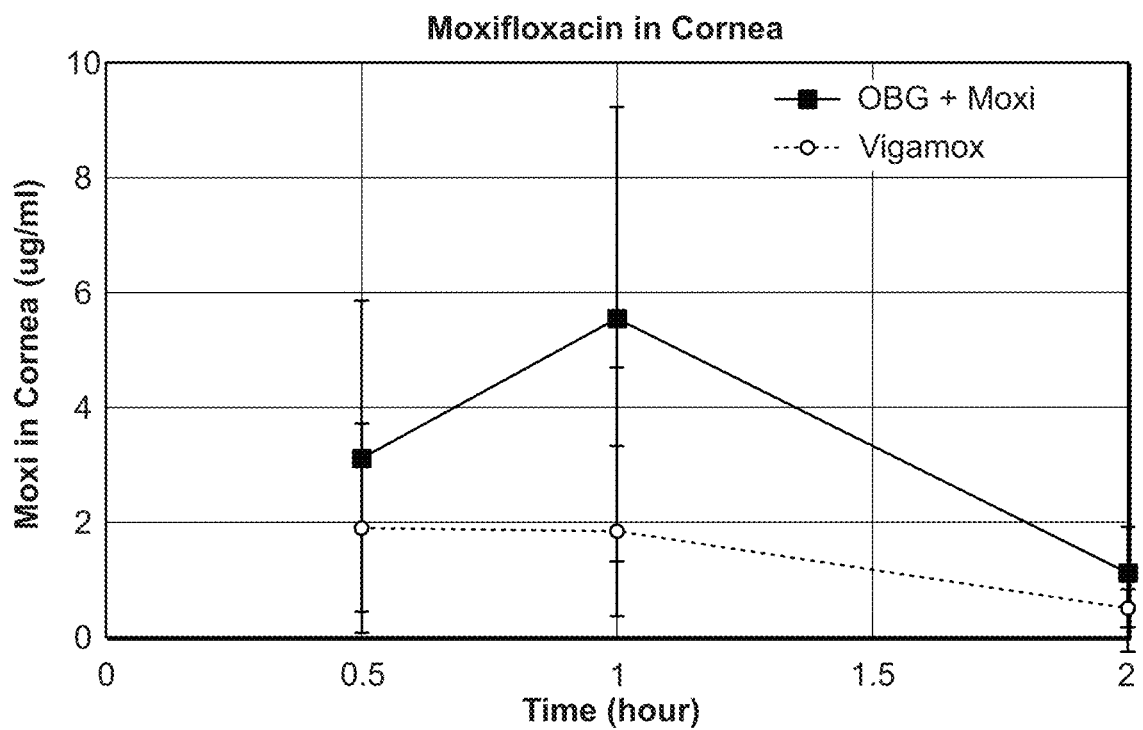
Figure 6C:
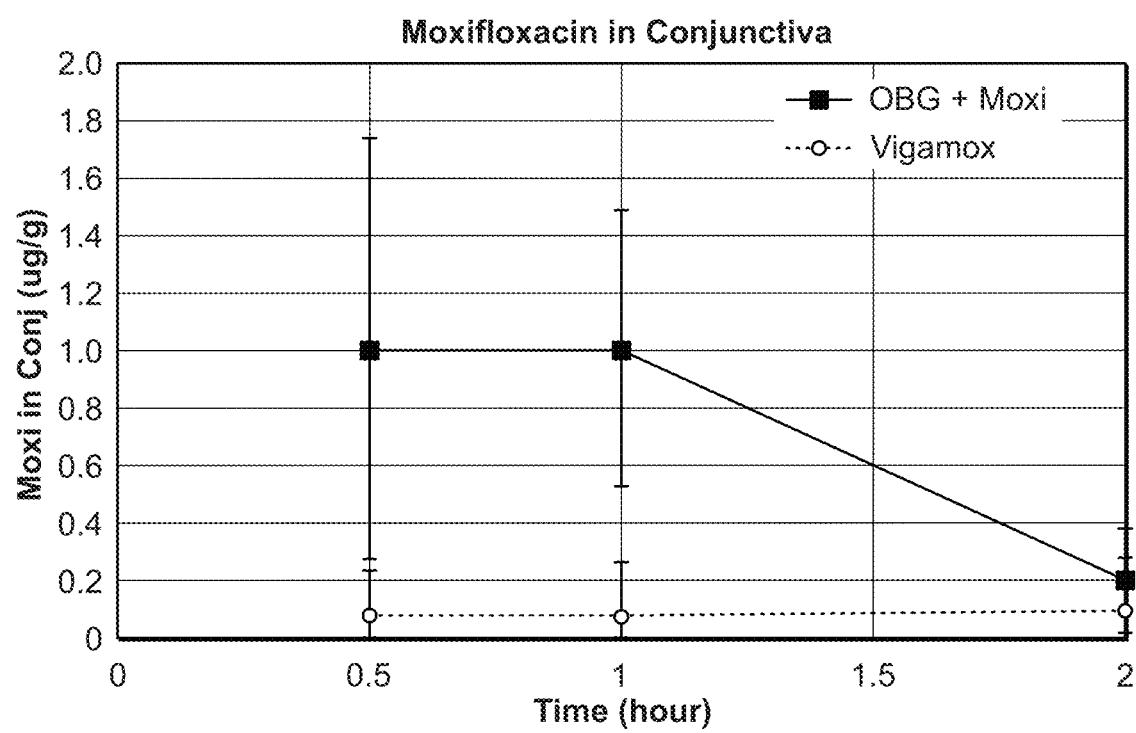

Moxifloxacin concentrations in the aqueous humor and cornea were comparable after administration of 0.15 mg/eye of moxifloxacin in the form of hydrogel+Moxi (Group 1) or Vigamox (Group 2) (FIGS. 6A and 6B). However, moxifloxacin levels were highest at 0.5 hr for Group 2 and 1 hr for Group 1. In conjunctiva, there was a higher concentration of moxifloxacin at 0.5 and 1 hr in Group 1 compared to Group 2 (FIG. 6C). These patterns suggest rapid availability of moxifloxacin to the ocular tissues following release from the hydrogel, and the drug concentrations were similar or slightly higher when using the hydrogel for drug delivery compared to a solution of drug.

This study indicates that a combined formulation of hydrogel+antibiotic can be used both to treat the ocular surface (such as a defect or ulcer) with the hydrogel and prevent infection with the antibiotic. The treatment schedule generally used for the antibiotic would not need to be altered to deliver the proper antibiotic dose.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

We claim:

1. An ocular composition, comprising:
   a shear-thinning hydrogel comprising a thiolated hyaluronic acid (HA), wherein the thiolated HA is at a concentration of about 3 to about 8 mg/ml and is covalently crosslinked, and a thiol modification of the thiolated HA is between about 0.05 to about 0.15 µmol thiol/mg; and
   an antibiotic at a concentration of about 1 to about 10 mg/ml,
   wherein the ocular composition is in the form of an eyedrop.

2. The ocular composition of claim 1, wherein the thiolated hyaluronic acid is at a concentration of about 3, 4, 5, 6, 7, or 8 mg/ml.

3. The ocular composition of claim 1, wherein the antibiotic is at a concentration of 1, 2, 3, 4, 5, 6, 7, 8, 9, or 10 mg/ml.

4. The ocular composition of claim 1, wherein the antibiotic has a solubility in water of about 1 mg/ml or greater.

5. The ocular composition of claim 1, wherein the antibiotic is a fluoroquinolone.

6. The ocular composition of claim 5, wherein the antibiotic is moxifloxacin or a salt of moxifloxacin.

7. The ocular composition of claim 6, wherein the antibiotic is moxifloxacin hydrochloride.

8. The ocular composition of claim 5, wherein the antibiotic is a salt of besifloxacin.

9. The ocular composition of claim 8, wherein the antibiotic is besifloxacin hydrochloride.

10. The ocular composition of claim 1, wherein the antibiotic is an aminoglycoside.

11. The ocular composition of claim 10, wherein the antibiotic is tobramycin.

12. The ocular composition of claim 1, wherein the thiolated hyaluronic acid is thiolated carboxymethyl hyaluronic acid.

13. The ocular composition of claim 1, wherein the hydrogel is disulfide crosslinked.

14. The ocular composition of claim 12, wherein the hydrogel is disulfide crosslinked.

15. An ocular composition, comprising:
    a shear-thinning hydrogel comprising thiolated hyaluronic acid (HA), wherein the thiolated HA is at a concentration of about 3 to about 8 mg/ml and is disulfide crosslinked, and a thiol modification of the thiolated HA is between about 0.05 to about 0.15 µmol thiol/mg; and
    an antibiotic at a concentration of about 1 to about 10 mg/ml,
    wherein upon application, the shear-thinning hydrogel resides on an eye of a patient for between about 30 minutes and about 2 hours, and
    wherein the ocular composition is in the form of an eyedrop.

16. The ocular composition of claim 15, wherein the thiolated hyaluronic acid is at a concentration of 3, 4, 5, 6, 7, or 8 mg/ml.

17. The ocular composition of claim 15, wherein the antibiotic is at a concentration of 1, 2, 3, 4, 5, 6, 7, 8, 9, or 10 mg/ml.

18. The ocular composition of claim 15, wherein the thiolated hyaluronic acid is at a concentration of about 6.5 to about 8.0 mg/ml.

19. The ocular composition of claim 15, wherein the antibiotic is a fluoroquinolone.

20. The ocular composition of claim 19, wherein the antibiotic is a salt of moxifloxacin.

21. The ocular composition of claim 20, wherein the antibiotic is moxifloxacin hydrochloride.

22. The ocular composition of claim 15, wherein the thiolated HA is thiolated carboxymethyl HA (CMHA-S).

23. The ocular composition of claim 22, which upon application remains in contact with an eye surface for at least 30 minutes and up to two hours.

24. The ocular composition of claim 22, wherein the CMHA-S is at a concentration of about 7 to about 8 mg/ml.

25. The ocular composition of claim 1, wherein the thiolated HA is at a concentration of about 7 to about 8 mg/ml.

26. The ocular composition of claim 1, wherein the thiolated HA is thiolated carboxymethyl HA (CMHA-S), and wherein the hydrogel has a viscosity of 0.9-3.6 Pa.s, measured at a shear rate of 2.5 Hz.

27. The ocular composition of claim 22, wherein the hydrogel has a viscosity of 0.9-3.6 Pa.s, measured at a shear rate of 2.5 Hz.

* * * * *